United States Patent [19]

Garbe et al.

[11] Patent Number: 5,688,523

[45] Date of Patent: Nov. 18, 1997

[54] METHOD OF MAKING A PRESSURE SENSITIVE SKIN ADHESIVE SHEET MATERIAL

[75] Inventors: James E. Garbe, Inver Grove Heights, Minn.; Paul J. Northey, Somerset, Wis.; Timothy A. Peterson, Lino Lakes, Minn.

[73] Assignee: Minnesota Mining and Manufacturing Company, St. Paul, Minn.

[21] Appl. No.: 414,721

[22] Filed: Mar. 31, 1995

[51] Int. Cl.$^6$ ............................................ A61F 13/00
[52] U.S. Cl. .................................... 424/448; 424/449
[58] Field of Search ............................. 424/448, 449

[56] References Cited

U.S. PATENT DOCUMENTS

| Re. 24,906 | 12/1960 | Ulrich | 206/59 |
|---|---|---|---|
| 4,714,655 | 12/1987 | Bordoloi et al. | 428/345 |
| 4,732,808 | 3/1988 | Krampe et al. | 428/355 |
| 4,737,559 | 4/1988 | Kellen et al. | 526/291 |
| 4,915,950 | 4/1990 | Miranda | 424/448 |
| 5,059,189 | 10/1991 | Cilento et al. | 604/307 |
| 5,110,599 | 5/1992 | Anhauser et al. | 424/449 |
| 5,126,144 | 6/1992 | Jaeger | 424/448 |
| 5,232,702 | 8/1993 | Pfister et al. | 424/448 |
| 5,264,224 | 11/1993 | Anhauser et al. | 424/467 |
| 5,350,581 | 9/1994 | Kochinke | 424/443 |
| 5,370,924 | 12/1994 | Kochinke | 428/224 |
| 5,626,866 | 5/1997 | Ebert et al. | 424/447 |

FOREIGN PATENT DOCUMENTS

| 072251 | 2/1983 | European Pat. Off. . |
|---|---|---|
| 0 219 762 | 4/1987 | European Pat. Off. . |
| 624635 | 11/1994 | European Pat. Off. . |
| 892499 | 10/1953 | Germany . |
| 40 16 808 | 1/1991 | Germany . |
| 42 30 589 | 2/1994 | Germany . |
| 43 32 094 | 3/1995 | Germany . |
| 2073588 | 10/1981 | United Kingdom . |

*Primary Examiner*—D. Gabrielle Phelan
*Attorney, Agent, or Firm*—Gary L. Griswold; Walter N. Kirn; Ted K. Ringsred

[57] ABSTRACT

A method of making a pressure sensitive skin adhesive sheet material whereby a coating medium involving a liquid and a polymer is applied to a base layer of a polymer, and the liquid is allowed to diffuse into the base layer.

27 Claims, 1 Drawing Sheet

METHOD OF MAKING A PRESSURE SENSITIVE SKIN ADHESIVE SHEET MATERIAL

BACKGROUND OF THE INVENTION

1. Field of the Invention

This invention relates to methods of making pressure sensitive skin adhesive sheet materials. More particularly this invention relates to methods of making pressure sensitive skin adhesive sheet materials containing a liquid. In another aspect this invention relates to methods of delivering a liquid to the skin.

2. Description of the Related Art

Pressure sensitive skin adhesives (PSAs) require a balance of viscous and elastic properties to afford adhesion, cohesion, stretchiness, and elasticity. PSAs have sufficient cohesiveness and elasticity so that despite their tackiness they can be handled with the fingers and removed from the skin without leaving substantial residue. Well known uses for PSAs include common adhesive strips and other wound dressings. They are also used in transdermal drug delivery devices.

A variety of transdermal drug delivery devices have been described. Devices known to the art include reservoir type devices involving membranes that control the rate of drug and/or skin penetration enhancer delivery to the skin, single layer devices involving a dispersion or solution of drug and excipients in an adhesive matrix, and more complex multi-laminate devices involving several distinct layers, e.g., layers for containing drug, for containing skin penetration enhancer, for controlling the rate of release of the drug and/or skin penetration enhancer, and for attaching the device to the skin.

When a transdermal drug delivery device incorporates a pressure sensitive skin adhesive layer comprising a dispersion or solution of drug and/or an excipient in a polymeric matrix, the adhesive layer typically is prepared by dissolving the polymer and the drug and/or excipient in a solvent, coating the resulting solution onto a web, then oven drying the coated web to evaporate the solvent. This conventional method has several disadvantages. When the drug and/or excipient is volatile or heat sensitive, the oven drying step can lead to loss of drug and/or excipient due to either evaporation or to thermal degradation. Also, this method requires a solvent based polymer, usually involving a volatile organic solvent.

Alternatively drug and/or excipient can be coated onto a release liner which is then laminated onto a polymeric layer in order to apply the drug and/or excipient to the polymeric layer. This method avoids the difficulties associated with heating of drug and/or excipient but nonetheless has disadvantages: uniformity of drug and/or excipient content is dependent on the relatively difficult process of coating the drug and/or excipient onto the low energy surface of the release liner, whereupon dewetting often occurs causing the ultimate distribution of the drug and/or excipient to be different from the distribution made in the coating process.

SUMMARY OF THE INVENTION

This invention provides a continuous method of making a pressure sensitive skin adhesive sheet material containing a liquid by combining a coating medium comprising said liquid with a polymeric base layer, which sheet material retains substantially all of the liquid until it is applied to the skin, comprising the steps of:

(i) providing a base layer of a first polymer, (ii) applying continuously to said base layer a coating medium comprising a second polymer dissolved or dispersed in a liquid and allowing the coating medium to diffuse into the base layer to provide a pressure sensitive skin adhesive sheet material.

This invention also provides a method of delivering a liquid to the skin, comprising steps (i) and (ii) above and the further step of (iii) applying the pressure sensitive skin adhesive sheet material from step (ii) to the skin without prior removal of a substantial amount of the liquid from the pressure sensitive skin adhesive sheet material.

In the manufacturing method of the invention the second polymer is used as a thickener in order to adjust the viscosity of the coating medium. This eliminates potential adverse affects that conventional thickeners (e.g., clay or silica gel) may have on adhesive properties of the ultimate product of the process. Furthermore, because the first and second polymers can be the same the manufacturing method of the invention does not require that an additional component be incorporated into the sheet material merely for the purpose of thickening the coating medium.

The manufacturing method of the invention eliminates the drying step required in some conventional methods, thus minimizing losses due to evaporation and/or thermal degradation. It also permits use of base layer polymers that are not based on an organic solvent thus eliminating all need for volatile organic solvents in manufacturing. Further, regardless of the type of polymer that is chosen for the base layer it can be processed prior to application of the coating medium, thus avoiding concerns arising out of physical or chemical instability of components of the coating medium (e.g., a drug or an excipient) to base layer processing conditions. For example, if the base layer polymer is solvent based, in order to remove residual solvent oven temperatures may be increased to well above those that could be tolerated by certain drugs, allowing increased line speeds when manufacturing a pressure sensitive skin adhesive containing such a drug.

While providing the advantages noted above this invention avoids the difficulties associated with the liner coating process described above, for the coating medium need not be put down over the low energy surface of a release liner.

DETAILED DESCRIPTION OF THE INVENTION

Figure 1:
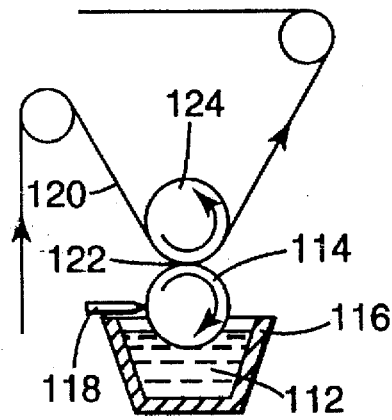
FIG. 1 is a schematic of direct gravure coating.

This invention provides a method for making a pressure sensitive skin adhesive sheet material containing a liquid, e.g., a liquid excipient that softens a non-adhesive or poorly adhesive polymer such that it can be used as a pressure sensitive skin adhesive. The pressure sensitive skin adhesive sheet materials prepared according to the process of the invention are particularly suitable for use in transdermal drug delivery devices involving liquid drugs or liquid excipients that affect adhesion, compliance, drug solubility, or the rate at which a drug penetrates the skin.

Step (i) of the manufacturing method of the invention provides a base layer comprising a first polymer. The first polymer can be, but need not be, a pressure sensitive skin adhesive by itself. As described in detail below certain polymers that are not suitable by themselves as adhesives may become suitably tacky upon addition of liquid softening agents. Such softening agents can be incorporated into the base layer polymer at the outset or they may be added in step (ii) of the process of the invention. In any event the first polymer is a polymer that can be used as the basis for a pressure sensitive skin adhesive. It is preferably dermatologically and pharmaceutically acceptable and substantially chemically inert to any drug and/or excipient that is later to be incorporated. Examples of suitable polymers include addition polymers, e.g., acrylates such as those disclosed, for example, in U.S. Pat. No. RE 24,906 (Ulrich), U.S. Pat. No. 4,732,808 (Krampe et al.), the disclosures of which are incorporated herein by reference, and those disclosed in commonly assigned copending application Ser. No. 08/305,833 (Garbe et al.), adhesives, polyisobutylenes, polyisoprenes, styrene block copolymers (e.g., SEBS copolymers, SBS copolymers), and the like, and condensation polymers such as those used as silicone adhesives as disclosed in U.S. Pat. No. 5,232,702 (incorporated by reference). Generally the base layer is about 25–600 μm thick.

The base layer can be carded on a substrate, which preferably is substantially chemically inert and physically inert to the components to be applied thereto (e.g., it does not react chemically with such components, nor does it absorb or swell with such components). Examples of suitable substrates include backing films, release liners, differential release liners (i.e., liners in which both sides have release properties but one surface releases more readily than the opposing surface), and membranes.

Suitable backing films for use as the substrate include conventional flexible backing materials used for pressure sensitive adhesive tapes, such as polyethylene, particularly low density polyethylene, linear low density polyethylene, high density polyethylene, polyester such as polyethylene terephthalate, randomly oriented nylon fibers, polypropylene, ethylene:vinyl acetate copolymers, polyurethane, rayon, and the like. Backings that are layered, such as polyethylene-polyester-aluminumpolyethylene composites, are also suitable.

Suitable release liners for use as a substrate include conventional release liners comprising a known sheet material such as a polyester web, a polyethylene web, or a polystyrene web, or a polyethylene-coated paper, coated with a suitable fluoropolymer or silicone based coating. Suitable differential release liners include conventional differential release liners comprising a known sheet material such as a polyester web, a polyethylene web, or a polystyrene web, or a polyethylene-coated paper, coated on both surfaces with suitable fluoropolymer or silicone based coatings. Examples of suitable materials for use in membranes include polyethylene, low density polyethylene, linear low density polyethylene, high density polyethylene, polyurethane, nylon, and ethylene:vinyl acetate copolymers. Examples of suitable physical forms for the membranes include continuous film, macroporous membrane, and microporous membrane.

Selection of a substrate depends on the steps involved in the overall manufacturing process of the pressure sensitive skin adhesive sheet material and on the configuration of the final product (e.g., a transdermal drug delivery device) that incorporates the sheet material. For example, if the base layer is manufactured off line and stored as rollstock, then a differential release liner is a preferred substrate. Alternatively, if the base layer is manufactured on line just prior to application of a coating medium, then a backing film or a liner having a single release surface may be preferred depending on the configuration of the final product that incorporates the sheet material.

The base layer can be put down by any conventional coating method, for example, by die coating or by dissolving the polymer in a solvent, coating the resulting solution onto a substrate, then oven drying the coated substrate to evaporate the solvent. Hot-melt, water borne, or radiation curing processing methods can also be used to put down a base layer.

Step (ii) of the manufacturing process of the invention involves applying a coating medium to the base layer. The manufacturing method of the invention is a continuous method, i.e., the coating medium is applied to the base layer as it passes the application means with no intermittent cessation of the relative motion of the base layer with respect to the application means, as opposed to an indexed, incremental, or stepwise method whereby a unit area of the base layer is indexed into place, the coating medium is applied, and the indexing and coating process is repeated on further unit areas of the base layer. If desired the coating medium can be applied in a pattern (e.g., in a series of parallel lines along the length of the base layer, in a pattern defined by a patterned printing or coating roll, or a patterned coating die, or in a pattern created by a change in coating weight with time).

The coating medium comprises (a) a liquid and (b) a second polymer. In addition to the liquid and the second polymer, other components such as a solid drug or solid excipient can be incorporated into the coating medium.

The liquid is selected from those materials which are suitable for use as a component of a pressure sensitive skin adhesive and liquid at the operating temperature of the process and substantially atmospheric pressure. The operating temperature can be any temperature suitable to a coating process but is preferably a relatively low temperature (e.g., about 20°–50° C., more preferably about 20°–40° C.) such that the advantages of the process are retained with respect to thermally labile materials.

Liquid drugs, liquid excipients, and mixtures thereof can be used.

Examples of suitable liquid drugs include (S)-3-methyl-5-(1-methyl-2-pyrrolidinyl)isoxazole, nicotine, nitroglycerin, amyl nitrite, ethchlorvynol, paramethadione, scopolamine, and free bases of certain drugs that are conventionally used in the form of acid-addition salts.

Suitable liquid excipients include generally oily materials that raise the compliance value or lower the apparent glass transition temperature ($T_g$) of the polymer used as the base layer, including certain materials that have been used as skin penetration enhancers or solubilizers in transdermal drug delivery systems. Exemplary materials include $C_8$–$C_{22}$ fatty acids such as isostearic acid, octanoic acid, and oleic acid, $C_8$–$C_{22}$ fatty alcohols such as oleyl alcohol and lauryl alcohol, lower alkyl esters of $C_8$–$C_{22}$ fatty acids such as ethyl oleate, isopropyl myristate, butyl stearate, and methyl laurate, di(lower) alkyl esters of $C_6$–$C_8$ diacids such as diisopropyl adipate, monoglycerides of $C_8$–$C_{22}$ fatty acids such as glyceryl monolaurate, tetrahydrofurfuryl alcohol polyethylene glycol ether, polyethylene glycol, propylene glycol, 2-(2-ethoxyethoxy)ethanol, diethylene glycol monomethyl ether, and combinations of the foregoing. Alkylaryl ethers of polyethylene oxide, polyethylene oxide monomethyl ethers, and polyethylene oxide dimethyl ethers are also suitable, as are solubilizers such as dimethyl sulfoxide, glycerol, ethanol, ethyl acetate, acetoacetic ester, N-methyl pyrrolidone, and isopropyl alcohol.

Preferred liquid excipients include glyceryl monolaurate, diethylene glycol monomethyl ether, tetrahydrofurfuryl alcohol polyethylene glycol ether, diisopropyl adipate, propylene glycol, isopropyl myristate, ethyl oleate, methyl laurate, 2-(2-ethoxyethoxy)ethanol, and oleyl alcohol.

A second polymer is combined with the liquid to form the coating medium. Suitable second polymers include those enumerated above in connection with the base layer. The second polymer is preferably of the same chemical class (e.g., an acrylate or a styrene block copolymer, as the case may be) as the first polymer used in the base layer. More preferably the second polymer contains the same monomers, and most preferably it contains the same constituent monomers in the same ratios and is of the same inherent viscosity as the first polymer. The second polymer is selected such that it is capable of being dispersed and/or dissolved in the liquid. Generally, the liquid and the second polymer can be combined using any suitable technique that will form a solution or a dispersion of the second polymer in the liquid, including stirring, shaking, ultrasonic vibration, and the like. The liquid and the second polymer are combined and blended until a substantially homogeneous coating medium (that is, a coating medium wherein the second polymer is substantially uniformly distributed throughout the liquid bulk, e.g., in the form of a solution or a dispersion) is obtained. In a preferred embodiment of the invention the second polymer is soluble in the liquid, and the resulting coating medium is a solution.

The identity and relative mount of the liquid and polymer components incorporated into the coating medium, and the particular base layer polymer for a particular application can be readily determined by consideration of the structure and properties of the liquid, the first polymer, and the second polymer, along with the intended coating process and desired properties of the ultimate product pressure sensitive skin adhesive sheet material.

The properties desirable in a pressure sensitive skin adhesive are well known to those skilled in the art. For example, the adhesive should achieve and remain in intimate contact with the skin in order to adhere reliably and, if it incorporates a drug or penetration enhancer and is used in a transdermal drug delivery device, deliver to the skin at a stable rate. It is desirable for a pressure sensitive skin adhesive to have sufficiently little cold flow such that it is stable to flow upon storage. It is also preferred that it release cleanly from the skin. In order to achieve skin contact, clean release, preferred levels of adhesion, and resistance to cold flow, the mount and structure of the monomers in the base layer polymer, the inherent viscosity of the base layer polymer, and the mount and structure of the liquid and polymer components of the coating medium are preferably selected such that the resulting pressure sensitive skin adhesive has a compliance value (measured according to the test method set forth in detail below) in the range $1 \times 10^{-5}$ $cm^2/dyne$ to $5 \times 10^{-4}$ $cm^2/dyne$. Materials having compliance values outside this range are sometimes suitable for use as pressure sensitive skin adhesives. However, those having substantially lower compliance values will generally be relatively stiff and have less than optimal skin contact and adhesion to skin. Those having substantially higher compliance values will generally have less than optimal cold flow and might leave substantial residue when removed from the skin.

Particularly suitable compositions can be readily selected for a given set of desired properties considering the effects described below:

As regards the first polymer, that is, the polymer in the base layer, structural features can be tailored according to intended performance of the ultimate product of the process. For example, macromonomers such as those described in U.S. Pat. No. 4,732,808 (Krampe et al.) can be incorporated into acrylate polymers in order to decrease compliance of the base layer polymer compared to the compliance of a like acrylate base layer polymer without macromonomer. Strongly hydrogen bonding monomers have been found to increase the amount of polar or hydrogen bonding substances that can be dissolved in a polymer and to decrease the amount of generally nonpolar substances that can be dissolved. Further, a strongly hydrogen bonding copolymer will be a relatively less compliant material. Therefore if hydrogen bonding monomers such as acrylic acid or acrylamide are used in a base layer polymer a lesser amount of macromonomer will be required in order to lower compliance sufficiently to avoid cohesive failure.

A relatively high compliance pressure sensitive skin adhesive involving a macromonomer will generally have better adhesive properties than a macromonomer free polymer having the same compliance value. Increasing macromonomer content generally increases the amount of liquid excipient that can be loaded into a pressure sensitive skin adhesive without cohesive failure. Increasing inherent viscosity will also tend to allow higher loading with liquid excipient without cohesive failure.

A change that would increase inherent viscosity of a polymer (such as increased molecular weight through selection of polymerization conditions and/or solvent ratios) will generally decrease compliance.

As regards the second polymer, which is incorporated into the coating medium, it has been found that for some liquids at least a minimum mount of the second polymer must be used in order to obtain a coating medium that will wet the base layer of polymer. Substantially uniform wetting is preferred in order that the coating medium is substantially uniformly distributed over the desired surface of the base layer. The particular structure and amount of second polymer combined with the liquid is determined on the basis of the structure the polymer considering those parameters known to affect the flow mechanics of coating processes, such as solubility properties, the wetting relationship between the coating medium and the base layer, coating speed, viscosity of the coating medium, surface tension of the coating medium, and wet film thickness of the coating medium. Further, it is well known to those skilled in the art that rheological properties may render certain second polymers unsuitable for use in a particular coating medium due to the coating method to be used or the intended properties of the final product.

As regards the amount and identity of the liquid material, many of the liquids enumerated above are known to affect aspects of performance of pressure sensitive skin adhesives. Generally they are useful in softening or increasing the compliance value and/or lowering the glass transition temperature of otherwise non-compliant (and therefore poorly pressure sensitive adhesive) polymers, rendering them suitable for use as pressure sensitive skin adhesives. However, the liquids enumerated above are generally oily substances that function as plasticizers when incorporated in a polymer. Such materials can affect adversely the performance of a pressure sensitive skin adhesive, for example by softening it to the point of cohesive failure (where substantial polymer residue is left on the skin upon removal from the skin), or by separating from the continuous phase and forming an oily layer that reduces adhesion of an otherwise adhesive matrix. Also, when liquids phase separate from the base layer polymer, unstable properties (e.g., decreasing adhesion over time or unstable drug delivery rates in a transdermal drug delivery device) can result.

Given the several factors discussed above relating to selection of mounts and types of liquids and second polymers in the coating medium it is not practical to enumerate particular preferred mounts in connection with particular combinations, but such can be readily determined by those skilled in the an with due consideration of the relevant factors. Generally, however, the second polymer is present in the coating medium in an amount of about 0.5 to about 30 percent, preferably about 1 to 20 percent, by weight based on the total weight of the coating medium.

The amount of coating medium to be applied to the base layer is generally not more than that amount which causes the product pressure sensitive skin adhesive sheet material to lose adhesion or leave substantial residue on the skin when peeled from the skin. Depending upon the identity of the base layer polymer and the liquid, high loadings, e.g., up to and in excess of 40% by weight based on the total weight of the final pressure sensitive skin adhesive, can be achieved. In the event that the liquid comprises a drug it is applied such that the drug is present in a therapeutically effective amount, which varies from drug to drug but can be readily determined by those skilled in the art considering the particular drug, other excipients, and the particular intended therapeutic effect.

The method used to apply the coating medium to the base layer can be any method that is capable of putting a precise amount of coating medium in a uniform fashion onto the base layer. Suitable continuous methods include die coating, reverse gravure and forward gravure coating. Particularly preferred methods, which are described in detail below, include direct gravure coating, kiss gravure coating, and extrusion die coating.

Gravure coating uses a gravure roll having etched, machined, or knurled recesses on its surface. The coating medium is transferred from the recesses to the layer to be coated. The recesses may be of any size or shape, discontinuous over the surface, or as used here, continuous over the surface of the roll. A common pattern for continuous coatings is a trihelical pattern consisting of diagonal triangular grooves on the roll surface.

FIG. 1 shows a schematic of direct gravure coating. Coating medium 112 is supplied to gravure roll 114 by means of pan 116. The volume of coating medium 112 in the recesses of gravure roll 114 is then adjusted by means of doctor blade 118. Coating medium 112 is coated on to base layer 120 comprising the first polymer at nip point 122 by contacting base layer 120 with the coating medium contained in the recesses of gravure roll 114 by means of impression roll 124. Factors that have been found to influence coating weight (i.e., the mount of coating medium that is applied per unit area of base layer) and/or coating uniformity include certain gravure roll parameters, identity of the liquid material, viscosity of the coating medium, line speed, nip pressure and gravure roll/line speed ratio. The gravure roll parameter of particular importance is the volume factor, i.e., the internal recess volume per unit area of the gravure roll surface. A change in any of these factors can affect coating weight and/or coating uniformity.

Figure 2:
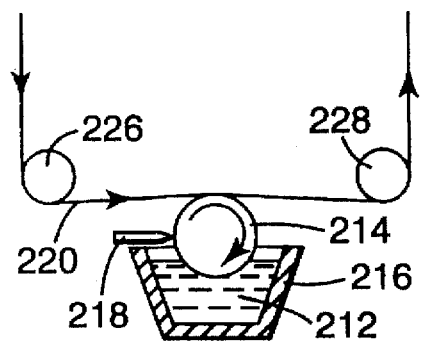
FIG. 2 is a schematic of kiss gravure coating.

FIG. 2 shows a schematic of kiss gravure coating. Coating medium 212 is supplied to gravure roll 214 by means of pan 216. The volume of coating medium 212 in the recesses of gravure roll 214 is then adjusted by means of doctor blade 218. Base layer 220 comprising the first polymer is brought into contact with the gravure roll by positioning input idler roll 226 and output idler roll 228 to create a slight wrap over gravure roll 214. Factors that have been found to influence coating weight and/or coating uniformity include certain gravure roll parameters, identity of the liquid material, viscosity of the coating medium, line speed, and gravure roll/line speed ratio. The gravure roll parameter of particular importance is the volume factor. A change in any of these factors can affect the coating weight and/or uniformity.

Figure 3:
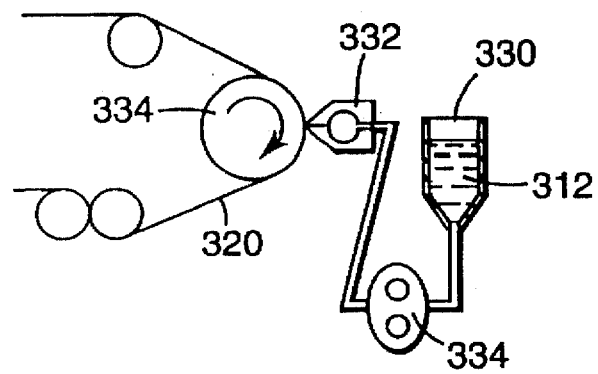
FIG. 3 is a schematic of extrusion die coating.

FIG. 3 shows a schematic of extrusion die coating. Coating medium 312 is placed in feed hopper 330 and from there it is supplied to extrusion die 332 by means of metering pump 334. Base layer 320 comprising the first polymer is brought through the space between back-up roll 334 and extrusion die 332, and extrusion die 332 distributes coating medium 312 across base layer 320. Factors that have been found to influence coating weight and/or coating uniformity include identity of the liquid material, viscosity of the coating medium, line speed, pump speed, and the amount of space between the extrusion die and the back-up roll. Die coating provides several advantages: good crossweb uniformity; the use of a metering pump provides means for delivering an accurate amount of coating medium; and the coating medium is enclosed until it is coated, which reduces the risk of evaporation or degradation caused by exposure to the atmosphere.

After coating the liquid is allowed to diffuse into the base layer until the product is sufficiently dry for lamination or wind-up. The length of time that this takes is dependent on the coating weight and the type of base layer polymer and second polymer, but generally takes only a few (e.g., 1–3) minutes.

The method of the invention optionally comprises the further step of laminating the exposed surface of the pressure sensitive skin adhesive sheet material from step (ii) to a substrate. Examples of suitable substrates include those enumerated above in connection with the substrate that carries the base layer. The preferred substrate depends on the configuration of the final product incorporating the sheet material. For example, if the final product is a matrix drug-in-adhesive transdermal drug delivery device and the base layer is carded on a release liner, then a backing film could be laminated to the exposed surface of the sheet material to provide a composite that could be die cut into the desired devices. Alternatively, if the sheet material is part of a complex multilaminate device then a membrane may be the chosen substrate.

The sheet material from step (ii) can also be laminated to a layer of pressure sensitive skin adhesive that optionally comprises drug and/or excipient.

A pressure sensitive skin adhesive sheet material made according to the manufacturing method of the invention retains substantially all of the liquid until it is applied to the skin, i.e., the liquid is not intentionally substantially completely removed from the sheet material by a process such as evaporation or extraction. In the case of a volatile liquid, however, some amount might be removed incidentally due to storage or exposure of the sheet material to elevated temperatures during processing, such as might be encountered in a manufacturing facility on a hot day. In any event retention of substantially all of the liquid means that at least about two-thirds of the liquid, more preferably at least about four-fifths of the liquid, even more preferably at least about nine-tenths of the liquid, and most preferably at least about 95 percent of the liquid, is retained in the device until it is applied to the skin.

In the method of the invention for delivering a liquid to the skin, a pressure sensitive skin adhesive sheet material prepared according to the above-described process is applied to the skin without prior removal of a substantial amount of the liquid from the pressure sensitive sheet material, e.g., by volatilization or extraction, as described immediately above. When a volatile liquid is delivered volatilization can be inhibited by overlaying the pressure sensitive skin adhesive sheet material on both surfaces with a sheet material such as a backing or release liner that is substantially impermeable to the vaporized liquid.

Compliance Test Method

Compliance values can be obtained using a modified version of the Creep Compliance Procedure described in U.S. Pat. No. 4,737,559 (Kellen), the disclosure of which is incorporated herein by reference. The release liner is removed from a sample of the material to be tested. The exposed adhesive surface is folded back on itself in the lengthwise direction to produce a "sandwich" configuration, i.e., backing/adhesive/backing. The "sandwiched" sample is passed through a laminator, or alternatively rolled with a hand-operated roller, then two test samples of equal area are cut using a rectangular die. One test sample is centered on the stationary plate of a shear-creep rheometer with the long axis of the test sample centered on the short axis of the plate. The small non-stationary plate of the shear-creep rheometer is centered over the first sample on the stationary plate such that the hook is facing up and toward the front of the rheometer. The second test sample is centered on the upper surface of the small non-stationary plate matching the axial orientation of the first test sample. The large stationary plate is placed over the second test sample and the entire assembly is clamped into place. The end of the small non-stationary plate that is opposite the end with the hook is connected to a chart recorder. A string is connected to the hook of the small non-stationary plate and extended over the from pulley of the rheometer. A weight (e.g., 500 g) is attached to the free end of the string. The chart recorder is started and at the same time the weight is quickly released so that it hangs free. The weight is removed after exactly 3 minutes has elapsed. The displacement is read from the chart recorder. The compliance is then calculated using the equation:

$$J = 2\frac{AX}{hf}$$

where A is the area of one face of the test sample, h is the thickness of the adhesive mass (i.e., two times the matrix thickness of the sample being tested), X is the displacement and f is the force due to the mass attached to the string. Where A is expressed in $cm^2$, h in cm, X in cm and f in dynes, the compliance value is given in $cm^2/dyne$.

The examples set forth below are intended to illustrate the invention.

EXAMPLE 1

A base layer was prepared in the following manner. An adhesive solution (74:6:20 isooctyl acrylate:acrylamide:vinyl acetate copolymer, 22 percent solids in 91:9 ethyl acetate:methanol, inherent viscosity=1.21 dl/g) was extrusion die coated onto the non-release side of a silicone coated polyethylene terephthalate (PET) release liner (Daubert). The die was equipped with a 20 mil (500 μm) shim. The coated release liner was oven dried at 150° F. (65° C.) for 1 minute, at 275° F. (135° C.) for 1 minute and at 350° F. (177° C.) for 1 minute. Four thousand (4,000) linear yards (3640 linear meters) of web with a width of 7 inches (17.8 cm) was produced.

A coating medium was prepared by dissolving 20 percent by weight of 94:6 isooctyl acrylate:acrylic acid adhesive copolymer in isopropyl myristate. The resulting medium had a Brookfield viscosity of 1400 centipoise.

This coating medium was applied at a line speed of 10 feet/min (3.0 meter/min) to the base layer using direct gravure coating [gravure roll parameters: pattern—trihelical; 45 line per inch (18 lines per cm); volume factor—$3.0 \times 10^{-3}$ $in^3/in^2$ ($7.6 \times 10^{-3}$ $cm^3/cm^2$)]. A web measuring 6.5 inches (16.5 cm) by 20 to 50 feet (6.1–15.2 m) was prepared. Sections measuring 2 in by 12 in (5.08 cm by 30.48 cm) were cut from the web lengthwise at three different positions designated North (along one edge of the web), South (along the opposite edge of the web), and Center (down web from and between the North and South samples) and weighed. The weight of coating medium applied to each section was determined by subtracting the weight of the base layer from the total weight of each section. The results are shown in Table 1 below.

EXAMPLES 2–12

Using the method of Example 1, a series of pressure sensitive skin adhesive sheet materials containing isopropyl myristate (IPM) was prepared. Table 1 shows the composition of the coating medium, the Brookfield viscosity of the coating medium, the line speed, and the weight of coating medium applied. In all examples, the polymer used to prepare the coating medium was 94:6 isooctyl acrylate-:acrylic acid adhesive copolymer; the base layer was that prepared in Example 1 and the coating medium was applied using direct gravure coating employing the gravure roll described in Example 1.

TABLE 1

| Example Number | Coating Medium | Viscosity (cps) | Line Speed (m/min) | Coating Weight (mg/10 cm²) North | Center | South |
|---|---|---|---|---|---|---|
| 1 | 20% polymer in IPM | 1400 | 3.0 | 22.23 | 21.43 | 21.98 |
| 2 | 20% polymer in IPM | 1400 | 7.6 | 18.29 | 17.96 | 19.17 |
| 3 | 20% polymer in IPM | 1400 | 15.2 | 9.38 | 10.00 | 8.16 |
| 4 | 10% polymer in IPM | 275 | 3.0 | 28.30 | 25.70 | 26.12 |
| 5 | 10% polymer in IPM | 275 | 7.6 | 25.91 | 25.03 | 22.02 |
| 6 | 10% polymer in IPM | 275 | 15.2 | 23.86 | 21.18 | 21.31 |
| 7 | Polymer in IPM[1] | 163 | 3.0 | 31.52 | 30.81 | 33.74 |
| 8 | Polymer in IPM[1] | 163 | 7.6 | 25.62 | 23.15 | 25.87 |
| 9 | Polymer in IPM[1] | 163 | 15.2 | 19.42 | 18.25 | 19.93 |
| 10 | Polymer in IPM[2] | 60 | 3.0 | 36.63 | 37.38 | 37.79 |
| 11 | Polymer in IPM[2] | 60 | 7.6 | 34.07 | 33.32 | 34.70 |
| 12 | Polymer in IPM[2] | 60 | 15.2 | 28.80 | 30.73 | 31.98 |
| Control | IPM | 4 | 3.0 | Coating weights were not measured because the coatings were not uniform | | |
| Control | IPM | 4 | 15.2 | Coating weights were not measured because the coatings were not uniform | | |

[1],[2] Polymer amount not measured; amount used was that amount needed to obtain the indicated viscosity.

EXAMPLES 13–23

Using the method of Example 1, a series of pressure sensitive skin adhesive sheet materials containing nicotine was prepared. Table 2 shows the composition of the coating medium, the Brookfield viscosity of the coating medium, the coating method (either direct or kiss gravure coating), the line speed, and the weight of coating medium applied. In all examples, the polymer used to prepare the coating medium was 74:6:20 isooctyl acrylate:acrylamide:vinylacetate adhesive copolymer; the base layer was that prepared in Example 1 and the coating medium was applied using the gravure roll described in Example 1. Attempts to uniformly coat nicotine neat, i.e. containing 0% polymer, failed.

TABLE 2

| Example Number | Coating Medium | Viscosity (cps) | Coating Method | Line Speed (m/min) | Coating Weight (mg/10 cm$^2$) North | Center | South |
|---|---|---|---|---|---|---|---|
| 13 | 10% polymer in nicotine | 892 | kiss | 3.0 | 38.18 | 35.41 | 37.21 |
| 14 | 10% polymer in nicotine | 892 | kiss | 7.6 | 32.94 | 29.97 | 32.02 |
| 15 | 10% polymer in nicotine | 892 | kiss | 15.2 | 28.13 | 27.33 | 28.38 |
| 16 | 10% polymer in nicotine | 892 | direct | 3.0 | 33.24 | 30.18 | 33.03 |
| 17 | 10% polymer in nicotine | 892 | direct | 6.1 | 34.66 | 31.94 | 34.16 |
| 18 | 7.5% polymer in nicotine | 340 | direct | 3.0 | 37.13 | 36.21 | 34.49 |
| 19 | 7.5% polymer in nicotine | 340 | direct | 7.6 | 32.02 | 31.10 | 31.27 |
| 20 | 5% polymer in nicotine | 136 | direct | 7.6 | 33.91 | 31.06 | 31.35 |
| 21 | 2.5% polymer in nicotine | 38 | direct | 3.0 | 34.53 | 32.27 | 31.40 |
| 22 | 2.5% polymer in nicotine | 38 | direct | 7.6 | 31.48 | 31.69 | 29.13 |
| 23 | 2.5% polymer in nicotine | 38 | direct | 15.2 | 32.24 | 30.39 | 29.80 |

EXAMPLE 24

A coating medium was prepared by dissolving 5% by weight of 74:6:20 isoocyl acrylate:acrylamide:vinyl acetate adhesive copolymer in nicotine. The resulting coating medium was applied to 60 linear yards (54.6 linear meters) of the base layer prepared in Example 1 using direct gravure coating with the gravure roll used in Example 1 at a line speed of 3 m/min. The down web/cross web uniformity was evaluated as follows. Samples 1–3 were taken every 1 linear yard (0.9 m) from the end of the web. Approximately 20 linear yards (18 m) of web were skipped over then samples 4–20 were taken every 2 linear yards (1.8 linear meters). Each sample consisted of 4 cross web 10 cm$^2$ patches labeled A–D. The patches were extracted with ethyl acetate and the extract analyzed for nicotine by gas chromatography. The results are shown in Table 3 below.

TABLE 3

| Sample | Nicotine Content (mg/patch) A | B | C | D |
|---|---|---|---|---|
| 1 | 36.3 | 36.3 | 36.0 | 34.9 |
| 2 | 36.3 | 36.1 | 35.7 | 35.5 |
| 3 | 36.3 | 36.0 | 35.6 | 35.0 |
| 4 | 36.9 | 35.9 | 35.6 | 34.8 |
| 5 | 36.8 | 36.3 | 36.3 | 35.1 |
| 6 | 36.2 | 36.8 | 36.6 | 35.5 |
| 7 | 35.2 | 36.5 | 36.6 | 36.6 |
| 8 | 23.8 | 36.5 | 36.3 | 35.4 |
| 9 | 36.2 | 36.5 | 36.5 | 35.6 |
| 10 | 37.1 | 36.7 | 36.3 | 35.1 |
| 11 | 35.6 | 36.4 | 36.3 | 35.1 |
| 12 | 25.0 | 36.3 | 36.2 | 35.4 |
| 13 | 36.8 | 36.2 | 34.7 | 23.7 |
| 14 | 36.2 | 36.1 | 35.2 | 34.4 |
| 15 | 36.0 | 36.2 | 34.2 | 34.9 |
| 16 | 35.2 | 34.6 | 35.4 | 34.7 |
| 17 | 35.8 | 36.3 | 35.6 | 35.1 |
| 18 | 35.8 | 34.4 | 35.2 | 34.1 |
| 19 | 35.2 | 34.9 | 34.4 | 32.7 |
| 20 | 34.3 | 36.0 | 34.9 | 33.6 |

EXAMPLES 25–35

A coating medium was prepared by dissolving 2.5% by weight of 74:6:20 isooctyl acrylate:acrylamide:vinyl acetate adhesive copolymer in nicotine. The resulting coating medium was applied to about 20 linear feet (6.1 linear meters) of the base layer prepared in Example 1 using kiss gravure coating (gravure roll parameters: pattern—pyramidal; volume factor—2.0×10$^{-3}$ in$^3$/in$^2$ (5×10$^{-3}$ cm$^3$/cm$^2$). During the coating process both the line speed and the gravure roll speed were varied. Table 4 below shows the line speed, the gravure roll:line speed ratio and the coating weight.

TABLE 4

| Example Number | Line Speed (m/min) | Ratio | Coating weight (mg/10 cm$^2$) North | Center | South |
|---|---|---|---|---|---|
| 25 | 2.9 | 0.74 | 19.30 | 16.20 | 18.33 |
| 26 | 2.9 | 1.16 | 18.33 | 19.55 | 19.51 |
| 27 | 2.9 | 1.37 | 20.39 | 19.26 | 20.97 |
| 28 | 2.9 | 1.89 | 21.60 | 21.18 | 22.06 |
| 29 | 2.9 | 3.16 | 20.30 | 18.29 | 20.85 |
| 30 | 7.6 | 0.80 | 21.98 | 20.18 | 22.10 |
| 31 | 7.6 | 1.00 | 22.77 | 23.15 | 25.62 |
| 32 | 7.6 | 1.24 | 21.85 | 21.52 | 23.32 |
| 33 | 7.6 | 1.48 | 22.27 | 20.34 | 22.31 |
| 34 | 7.6 | 1.92 | 21.89 | 21.22 | 22.60 |
| 35 | 7.6 | 3.40 | 20.68 | 18.71 | 20.68 |

EXAMPLES 36–48

Using the method of Example 1, a series of pressure sensitive skin adhesive sheet materials containing (S)-3-methyl-5-(1-methyl-2-pyrrolidinyl)isoxazole was prepared. Table 5 shows the weight percent of polymer in the coating medium, the Brookfield viscosity of the coating medium, the line speed, and the weight of coating medium applied. In all examples, the polymer used to prepare the coating medium was 74:6:20 isooctyl acrylate:acrylamide:vinylacetate adhesive copolymer; the base layer was that prepared in Example 1 and the coating medium was applied using kiss gravure coating (gravure roll parameters: pattern—pyramidal; volume factor—2.0×10$^{-3}$ in$^3$/in$^2$ (5×10$^{-3}$ cm$^3$/cm$^2$).

TABLE 5

| Example Number | Wt % Polymer | Viscosity (cps) | Line Speed (m/min) | Coating Weight (mg/10 cm$^2$) North | Center | South |
|---|---|---|---|---|---|---|
| 36 | 5.00 | 179 | 3.0 | 22.52 | 23.06 | 23.36 |
| 37 | 5.00 | 179 | 5.5 | 28.21 | 26.16 | 27.17 |
| 38 | 5.00 | 179 | 7.6 | 27.33 | 26.08 | 26.45 |
| 39 | 3.75 | 88 | 3.0 | 24.20 | 23.32 | 24.15 |
| 40 | 3.75 | 88 | 7.6 | 25.83 | 24.40 | 25.03 |
| 41 | 3.75 | 88 | 15.2 | 25.28 | 23.65 | 24.53 |
| 42 | 2.50 | 35 | 3.0 | 19.55 | 18.50 | 19.72 |
| 43 | 2.50 | 35 | 5.5 | 22.73 | 19.63 | 22.44 |
| 44 | 2.50 | 35 | 7.6 | 24.53 | 23.06 | 24.11 |
| 45 | 2.50 | 35 | 15.2 | 25.87 | 24.40 | 26.12 |
| 46 | 1.25 | 19 | 3.0 | 15.70 | 15.61 | 16.20 |
| 47 | 1.25 | 19 | 7.6 | 19.76 | 19.38 | 19.72 |
| 48 | 1.25 | 19 | 15.2 | 23.27 | 22.48 | 23.36 |
| Control | 0 | 5 | 3.0 | 13.02 | 12.60 | 13.52 |
| Control | 0 | 5 | 7.6 | 15.70 | 14.44 | 14.94 |
| Control | 0 | 5 | 15.2 | 16.58 | 15.91 | 16.66 |

EXAMPLES 49–53

Using the method of Example 1, a series of pressure sensitive skin adhesive sheet materials containing (S)-3-methyl-5-(1-methyl-2-pyrrolidinyl)isoxazole was prepared. Table 6 shows the weight percent of polymer in the coating medium, the Brookfield viscosity of the coating medium, the line speed, and the weight of coating medium applied. In all examples, the polymer used to prepare the coating medium was 74:6:20 isooctyl acrylate: acrylamide:vinylacetate adhesive copolymer; the base layer was that prepared in Example 1 and the coating medium was applied using kiss gravure coating (gravure roll parameters: pattern—trihelical; volume factor—2×10$^{-3}$ in$^3$/in$^2$, 5×10$^{-3}$ cm$^3$/cm$^2$).

TABLE 6

| Example Number | Weight % Polymer | Viscosity (cps) | Line Speed (m/min) | Coating Weight (mg/10 cm$^2$) North | Center | South |
|---|---|---|---|---|---|---|
| 49 | 3.75 | 88 | 3.0 | 23.36 | 23.19 | 23.11 |
| 50 | 3.75 | 88 | 7.6 | 24.32 | 25.62 | 26.66 |
| 51 | 1.25 | 19 | 3.0 | 18.63 | 17.16 | 19.30 |
| 52 | 1.25 | 19 | 5.5 | 22.40 | 18.38 | 21.47 |
| 53 | 1.25 | 19 | 7.6 | 21.93 | 20.26 | 21.81 |

EXAMPLE 54

A pressure sensitive skin adhesive sheet material containing (S)-3-methyl-5-(1-methyl-2-pyrrolidinyl)isoxazole was prepared in the following manner. A coating medium having a viscosity of 35 cps was prepared by dissolving 2.5 percent by weight of 74:6:20 isooctyl acrylate:acrylamide:vinylacetate adhesive copolymer in (S)-3-methyl-5-(1-methyl-2-pyrrolidinyl)isoxazole. The resulting coating medium was applied to 60 linear yards (54.6 linear meters) of the base layer prepared in Example 1 using kiss gravure coating [gravure roll parameters: pattern—pyramidal; 50 teeth per inch (20 teeth per cm); helix angle of 45 degrees; inclusion angle of 110 degrees; volume factor—2×10$^{-3}$ in$^3$/in$^2$ (5×10$^{-3}$ cm$^3$/cm$^2$)] at a line speed of 25 fpm (7.6 m/min). The down web/cross web uniformity of the resulting web was evaluated as follows. Four (4) cross web patches (10 cm$^2$ each) were die cut every 3 yards (2.7 m) for a total of 80 patches. The patches were extracted with ethyl acetate and the extract was assayed for (S)-3-methyl-5-(1-methyl-2-pyrrolidinyl)isoxazole (drug) content using gas chromatography. The results are shown in Table 7 below.

TABLE 7

| Down/cross | Drug Content (mg/patch) A | B | C | D | Average |
|---|---|---|---|---|---|
| 1 | 22.1 | 22.5 | 22.9 | 22.9 | 22.6 |
| 2 | 23.3 | 23.0 | 23.4 | 23.4 | 23.3 |
| 3 | 23.1 | 23.4 | 23.5 | 23.7 | 23.4 |
| 4 | 23.6 | 23.7 | 23.4 | 24.0 | 23.7 |
| 5 | 23.7 | 23.6 | 23.6 | 23.5 | 23.6 |
| 6 | 23.6 | 23.7 | 23.6 | 24.0 | 23.7 |
| 7 | 24.0 | 23.9 | 23.8 | 23.3 | 23.8 |
| 8 | 23.6 | 23.8 | 23.9 | 24.1 | 23.9 |
| 9 | 23.5 | 23.5 | 23.7 | 23.7 | 23.6 |
| 10 | 23.5 | 24.1 | 23.9 | 23.9 | 23.9 |
| 11 | 23.3 | 23.3 | 23.5 | 23.8 | 23.5 |
| 12 | 23.2 | 23.3 | 23.7 | 23.4 | 23.4 |
| 13 | 23.6 | 23.3 | 23.7 | 23.7 | 23.6 |
| 14 | 23.5 | 23.1 | 23.5 | 23.9 | 23.5 |
| 15 | 23.6 | 23.5 | 23.3 | 23.5 | 23.5 |
| 16 | 23.3 | 23.2 | 23.6 | 23.2 | 23.3 |
| 17 | 23.4 | 23.4 | 23.9 | 23.1 | 23.4 |
| 18 | 23.5 | 23.9 | 23.8 | 23.6 | 23.7 |
| 19 | 23.7 | 23.7 | 24.0 | 23.8 | 23.8 |
| 20 | 24.1 | 23.7 | 23.6 | 22.9 | 23.6 |
| Average | 23.4 | 23.5 | 23.6 | 23.6 | 23.5 |
| SD* | 0.40 | 0.37 | 0.26 | 0.35 | 0.28 |
| RSD** | 1.71 | 1.58 | 1.09 | 1.51 | 1.18 |

*Standard deviation
**Relative standard deviation

EXAMPLES 55–70

A series of pressure sensitive skin adhesive sheet materials containing (S)-3-methyl-5-(1-methyl-2-pyrrolidinyl) isoxazole was prepared in the following manner. A coating medium was prepared by dissolving 2.75 weight percent of 74:6:20 isooctyl acrylate: acrylamide:vinylacetate adhesive copolymer in (S)-3-methyl-5-(1-methyl-2-pyrrolidinyl) isoxazole. The resulting coating medium was applied using a gravure roll to the base layer prepared in Example 1. Table 8 below shows the gravure roll, the coating method, the line speed, the gravure roll speed and the coating weight. Gravure roll 1 had the following parameters: pattern—trihelical; 50 teeth per inch (20 teeth per cm); helix—45 degrees; inclusion angle –110 degrees; land width—0.0056 in (0.0142 cm); Z depth—0.0049 in (0.0124 cm); volume factor —1.8×10$^{-3}$ in$^3$/in$^2$ (4.6×10$^{-3}$ cm$^3$/cm$^2$). Gravure roll 2 had the following parameters: pattern—trihelical; 70 teeth per inch (27.6 teeth per cm); helix—45 degrees; inclusion angle—120 degrees; land width—0.0045 in (0.0114 cm); Z depth—0.0026 in (0.0066 cm); volume factor—0.97×10$^{-3}$ in$^3$/in$^2$ (2.46×10$^{-3}$ cm$^3$/cm$^2$).

TABLE 8

| Example Number | Gravure Roll | Coating Method | Line Speed (m/min) | Gravure Roll (m/min) | Coating Weight (mg/10 cm$^2$) North | Center | South |
|---|---|---|---|---|---|---|---|
| 55 | 1 | Kiss | 4.6 | 4.6 | 19.72 | 20.29 | 20.85 |
| 56 | 1 | Kiss | 7.6 | 7.6 | 19.23 | 18.59 | 20.73 |
| 57 | 1 | Kiss | 10.7 | 10.7 | 17.90 | 17.92 | 18.64 |
| 58 | 1 | Kiss | 7.6 | 7.6 | 18.83 | 19.07 | 20.37 |
| 59 | 1 | Kiss | 7.6 | 9.1 | 19.35 | 20.88 | 20.33 |
| 60 | 1 | Kiss | 7.6 | 10.7 | 19.64 | 20.42 | 20.94 |
| 61 | 1 | Direct | 4.6 | 4.6 | 16.67 | 16.83 | 17.11 |

TABLE 8-continued

| Example Number | Gravure Roll | Coating Method | Line Speed (m/min) | Gravure Roll (m/min) | Coating Weight (mg/10 cm$^2$) North | Coating Weight (mg/10 cm$^2$) Center | Coating Weight (mg/10 cm$^2$) South |
| --- | --- | --- | --- | --- | --- | --- | --- |
| 62 | 1 | Direct | 7.6 | 7.6 | 17.32 | 18.41 | 17.99 |
| 63 | 1 | Direct | 10.7 | 10.7 | 17.54 | 18.49 | 18.63 |
| 64 | 2 | Kiss | 4.6 | 4.6 | 10.71 | 10.80 | 10.87 |
| 65 | 2 | Kiss | 7.6 | 7.6 | 10.31 | 9.19 | 11.26 |
| 66 | 2 | Kiss | 10.7 | 10.7 | 8.98 | 9.61 | 9.85 |
| 67 | 2 | Kiss | 7.6 | 7.6 | 9.74 | 9.54 | 10.11 |
| 68 | 2 | Kiss | 7.6 | 9.1 | 10.47 | 10.83 | 10.77 |
| 69 | 2 | Kiss | 7.6 | 10.7 | 10.55 | 10.12 | 11.55 |
| 70 | 2 | Kiss | 7.6 | 12.2 | 11.69 | 11.01 | 12.64 |

EXAMPLE 71

A pressure sensitive skin adhesive sheet material containing (S)-3-methyl-5-(1-methyl-2-pyrrolidinyl)isoxazole was prepared in the following manner.

Adhesive copolymer (75:5:20 isooctyl acrylate:acrylamide:vinyl acetate; 30.2 percent solids in ethyl acetate-:methanol (91:9)) was coated onto a 3 mil (76 μM) PET differential release liner (SILOX G1K/G4L from AKROSIL). The coated release liner was oven dried at 60° C. for 1 minute, at 121° C. for 1 minute, and at 177° C. for 1 minute to provide a base layer of pressure sensitive skin adhesive consisting of adhesive 6.90 mg/cm$^2$ supported on a differential release liner.

A portion of the dried adhesive was stripped from the liner and dissolved in (S)-3-methyl-5-(1-methyl-2-pyrrolidinyl) isoxazole to provide a coating medium containing 2.75 percent by weight of adhesive and having a Brookfield viscosity of 44 cps.

The coating medium was applied to the base layer using direct gravure coating at a line speed of 25 fpm (7.6 m/min) employing a gravure roll with the following parameters: pattern—trihelical; 50 teeth per inch (20 teeth per cm); helix—45 degrees; inclusion angle—110 degrees; land width—0.0056 in (0.0142 cm); Z depth—0.0049 in (0.0124 cm); volume factor—1.8×10$^{-3}$ in$^3$/in$^2$ (4.6×10$^{-3}$ cm$^3$/cm$^2$). The resulting coating weight was 1.84 mg/cm$^2$.

Approximately 2.4 minutes after the coating medium was applied to the base layer the resulting web was laminated to a polyester backing (Scotchpak™ 1109 polyester film laminate available from the 3M Company) to provide a composite designated as Composite A. Composite A consisted of, in order, a backing, a single layer of adhesive containing (S)-3-methyl-5-(1-methyl-2-pyrrolidinyl)isoxazole, and a differential release liner.

The release liner was removed from Composite A and the adhesive side was laminated to a second section of the coated web to provide Composite B. Composite B consisted of, in order, a backing, a double layer of adhesive containing (S)-3-methyl-5-(1-methyl-2-pyrrolidinyl)isoxazole, and a differential release liner.

EXAMPLE 72

A pressure sensitive skin adhesive sheet material containing (S)-3-methyl-5-(1-methyl-2-pyrrolidinyl)isoxazole was prepared in the following manner.

Adhesive copolymer (75:5:20 isooctyl acrylate:acrylamide:vinyl acetate; 30.2 percent solids in ethyl acetate-:methanol (91:9)) was coated onto a 3 mil (76 μM) PET differential release liner (SILOX G1K/G4L from AKROSIL). The coated release liner was oven dried at 60° C. for 1 minute, at 121° C. for 1 minute, and at 177° C. for 1 minute to provide a base layer of pressure sensitive skin adhesive consisting of adhesive 4.06 mg/cm$^2$ supported on a differential release liner.

The coating medium prepared in Example 71 was applied to the base layer using direct gravure coating at a line speed of 25 fpm (7.6 m/min) employing a gravure roll with the following parameters: pattern—trihelical; 70 teeth per inch (27.6 teeth per cm); helix—45 degrees; inclusion angle—120 degrees; land width—0.0045 in (0.0114 cm); Z depth—0.0026 in (0.0066 cm); volume factor—0.97×10$^{-3}$ in$^3$/in$^2$ (2.46×10$^{-3}$ cm$^3$/cm$^2$). The resulting coating weight was 1.08 mg/cm$^2$.

Approximately 2.4 minutes alter the coating medium was applied to the base layer the resulting web was laminated to a two sided corona treated low density polyethylene film to provide a composite designated as Composite C. Composite C consisted of, in order, a corona treated low density polyethylene film, a single layer of adhesive containing (S)-3-methyl-5-(1-methyl-2-pyrrolidinyl)isoxazole, and a differential release liner.

EXAMPLE 73

Preparation of a Transdermal Drug Delivery Device

A transdermal drug delivery device containing (S)-3-methyl-5-(1-methyl-2-pyrrolidinyl)isoxazole was prepared in the following manner. The differential release liner was removed from Composite B of Example 71 and the exposed adhesive side was laminated to the polyethylene surface of Composite C of Example 72 to provide a composite designated as Composite D. Composite D consisted of, in order from the top (i.e. skin distal) layer down, a backing film, a drug-in-adhesive reservoir containing (S)-3-methyl-5-(1-methyl-2-pyrrolidinyl)isoxazole, a low density polyethylene film, a skin-contacting drug-in-adhesive matrix containing (S)-3-methyl-5-(1-methyl-2-pyrrolidinyl)isoxazole, and a differential release liner. The composite was die cut into patches. The differential release liner is removed prior to applying the patch to skin.

EXAMPLES 74–78

A series of pressure sensitive skin adhesive sheet materials containing isopropyl myristate were prepared in the following manner.

A coating medium was prepared by dissolving 10 percent by weight of 91:9 isooctyl acrylate: N-vinylpyrrolidone adhesive copolymer in isopropyl myristate. An ultraviolet fluorescent dye (Uvitex) was also incorporated, at the weight percentage shown in Table 9, as a means of determining coating uniformity.

The coating medium was applied to a 50 μm thick base layer (91:9 isooctyl acrylate: N-vinylpyrrolidone adhesive copolymer) using an extrusion die. The line speed, pump speed, and wet coating thickness are shown in Table 9 below. In all instance a pump delivering 2.92 cc/rev was used.

The emitted light intensity was measured at 7 different points on the web by a fluorimeter which excited at 375 nm and collected at 435 nm for a spot size of approximately 2 cm$^2$. The light intensities are shown in Table 9 below.

TABLE 9

| Example Number | Dye Wt % | Line Speed (m/min) | Pump Speed (rpm) | Wet Thickness (μm) | Light Intensity Point 1 | Point 2 | Point 3 | Point 4 | Point 5 | Point 6 | Point 7 |
| --- | --- | --- | --- | --- | --- | --- | --- | --- | --- | --- | --- |
| 74 | 0.5 | 18.3 | 9 | 7 | 35.16 | 36.91 | 37.12 | 37.81 | 36.11 | 36.42 | 38.46 |
| 75 | 0.5 | 10.0 | 9 | 13 | 45.91 | 45.37 | 44.16 | 44.30 | 43.98 | 45.06 | 46.29 |
| 76 | 0.5 | 10.0 | 4.5 | 6.5 | 33.31 | 31.83 | 31.96 | 32.82 | 31.27 | 32.42 | 34.86 |
| 77 | 0.1 | 10.0 | 6 | 8.7 | 15.43 | 15.61 | 16.23 | 15.54 | 15.35 | 18.52 | 18.53 |
| 78 | 0.1 | 10.0 | 4.5 | 6.5 | 13.06 | 12.70 | 12.08 | 11.99 | 12.36 | 12.04 | 13.27 |

What is claimed is:

1. A continuous method &making a pressure sensitive skin adhesive sheet material containing a liquid by combining a coating medium comprising said liquid with a polymeric base layer, which sheet material retains substantially all of the liquid until it is applied to the skin, comprising the steps of:
   (i) applying to a substrate layer a base layer of a first polymer said first polymer selected from the group consisting of acrylate polymers, polyisobutylenes, polyisoprenes, styrene block copolymers and silicone adhesives,
   (ii) applying continuously directly to said base layer a coating medium comprising a second polymer selected from the group consisting of acrylate polymers, polyisobutylenes, polyisoprenes, styrene block copolymers and silicone adhesives dissolved or dispersed in a liquid and allowing the coating medium to diffuse into the base layer to provide a pressure sensitive skin adhesive sheet material.

2. A method according to claim 1 wherein the liquid comprises a liquid drug.

3. A method according to claim 2 wherein the liquid drug is selected from the group consisting of (S)-3-methyl-5-(1-methyl-2-pyrrolidinyl)isoxazole, nicotine, nitroglycerin, and scopolamine.

4. A method according to claim 2 wherein the liquid drug is selected from the group consisting of nicotine, nitroglycerin, and (S)-3-methyl-5-(1-methyl-2-pyrrolidinyl)isoxazole.

5. A method according to claim 2 wherein the liquid drug is (S)-3-methyl-5-(1-methyl-2-pyrrolidinyl)isoxazole.

6. A method according to claim 1 wherein the liquid comprises a substance that raises the compliance value of the base layer.

7. A method according to claim 1 wherein the liquid comprises a material selected from the group consisting of $C_8$–$C_{22}$ fatty acids, $C_8$–$C_{22}$ fatty alcohols, $C_1$–$C_4$ alkyl esters of $C_8$–$C_{22}$ fatty acids, di($C_1$–$C_4$) alkyl esters of $C_6$–$C_8$ dicarboxylic acids, monoglycerides of $C_8$–$C_{22}$ fatty acids, tetrahydrofurfuryl alcohol polyethylene glycol ether, polyethylene glycol, propylene glycol, 2-(2-ethoxyethoxy) ethanol, diethylene glycol monomethyl ether, alkylaryl ethers of polyethylene oxide, polyethylene oxide monomethyl ethers, polyethylene oxide dimethyl ethers, dimethyl sulfoxide, glycerol, ethanol, ethyl acetate, acetoacetic ester, N-methyl pyrrolidone, and isopropyl alcohol.

8. A method according to claim 1 wherein the liquid comprises a material selected from the group consisting of glyceryl monolaurate, diethylene glycol monomethyl ether, tetrahydrofurfuryl alcohol polyethylene glycol ether, diisopropyl adipate, propylene glycol, isopropyl myristate, ethyl oleate, methyl laurate, 2-(2-ethoxyethoxy)ethanol, and oleyl alcohol.

9. A method according to claim 1 wherein the liquid comprises isopropyl myristate.

10. A method according to claim 1 wherein the second polymer is an acrylate polymer.

11. A method according to claim 1 wherein the second polymer is present in the coating medium in an mount of about 0.5 percent to about 30 percent by weight based on the total weight of the coating medium.

12. A method according to claim 1 wherein the second polymer is present in the coating medium in an amount of about 1 percent to about 20 percent by weight based on the total weight of the coating medium.

13. A method according to claim 1 wherein the coating medium is a solution.

14. A method according to claim 1 wherein the coating medium is applied to the base layer using gravure coating.

15. A method according to claim 1 wherein the coating medium is applied to the base layer using direct gravure coating.

16. A method according to claim 1 wherein the coating medium is applied to the base layer using kiss gravure coating.

17. A method according to claim 1 wherein the coating medium is applied to the base layer using extrusion die coating.

18. A method according to claim 1 wherein the first polymer is an acrylate polymer.

19. A method according to claim 1 wherein the first polymer is a radiation cured polymer.

20. A method according to claim 1 wherein the first polymer is a hot melt polymer.

21. A method according to claim 1 wherein the first polymer and the second polymer are the same.

22. A method according to claim 1 wherein the first polymer is an acrylate polymer and the second polymer is an acrylate polymer.

23. A method according to claim 22 wherein the liquid comprises a liquid drug.

24. A method according to claim 22 wherein the liquid comprises a material selected from the group consisting of $C_8$–$C_{22}$ fatty acids, $C_8$–$C_{22}$ fatty alcohols, $C_1$–$C_4$ alkyl esters of $C_8$–$C_{22}$ fatty acids, di($C_1$–$C_4$) alkyl esters of $C_6$–$C_8$ dicarboxylic acids, monoglycerides of $C_8$–$C_{22}$ fatty acids, tetrahydrofurfuryl alcohol polyethylene glycol ether, polyethylene glycol, propylene glycol, 2-(2-ethoxyethoxy) ethanol, diethylene glycol monomethyl ether, alkylaryl ethers of polyethylene oxide, polyethylene oxide monomethyl ethers, polyethylene oxide dimethyl ethers, dimethyl sulfoxide, glycerol, ethanol, ethyl acetate, acetoacetic ester, N-methyl pyrrolidone, and isopropyl alcohol.

25. A method according to claim 23, wherein the liquid further comprises a material selected from the group consisting of $C_8$–$C_{22}$ fatty acids, $C_8$–$C_{22}$ fatty alcohols, $C_1$–$C_4$ alkyl esters of $C_8$–$C_{22}$ fatty acids, di($C_1$–$C_4$) alkyl esters of $C_6$–$C_8$ dicarboxylic acids, monoglycerides of $C_8$–$C_{22}$ fatty acids, tetrahydrofurfuryl alcohol polyethylene glycol ether, polyethylene glycol, propylene glycol, 2-(2-ethoxyethoxy) ethanol, diethylene glycol monomethyl ether, alkylaryl ethers of polyethylene oxide, polyethylene oxide monomethyl ethers, polyethylene oxide dimethyl ethers, dimethyl sulfoxide, glycerol, ethanol, ethyl acetate, acetoacetic ester, N-methyl pyrrolidone, and isopropyl alcohol.

26. A method according to claim 1 further comprising the step of laminating the exposed surface of the pressure sensitive skin adhesive sheet material to a second substrate.

27. A method of delivering a liquid to the skin, comprising the steps of (i) applying to a substrate layer a base layer of a first polymer said first polymer selected from the group consisting of acrylate polymers, polyisobutylenes, polyisoprenes, styrene block copolymers and silicone adhesives, (ii) applying continuously directly to said base layer a coating medium comprising a second polymer selected from the group consisting of acrylate polymers, polyisobutylenes, polyisoprenes, styrene block copolymers and silicone adhesives dissolved or dispersed in a liquid and allowing the coating medium to diffuse into the base layer to provide a pressure sensitive skin adhesive sheet material, and (iii) applying the pressure sensitive skin adhesive sheet material from step (ii) to the skin without prior removal of a substantial amount of the liquid from the pressure sensitive skin adhesive sheet material.

* * * * *